United States Patent [19]

Bryan et al.

[11] Patent Number: 5,162,077

[45] Date of Patent: * Nov. 10, 1992

[54] DEVICE FOR IN SITU CLEANING A FOULED SENSOR MEMBRANE OF DEPOSITS

[76] Inventors: Avron I. Bryan, 26 Country Club Rd., Cocoa Beach, Fla. 32931; Michael R. Cushman, 521 Brandonwood Rd., Kingsport, Tenn. 37662

[*] Notice: The portion of the term of this patent subsequent to Feb. 13, 2007 has been disclaimed.

[21] Appl. No.: 624,963

[22] Filed: Dec. 10, 1990

[51] Int. Cl.⁵ .................. G01N 27/27; G01N 27/333; G01N 27/404

[52] U.S. Cl. .................... 204/402; 204/415; 204/433; 204/153.17; 204/153.21; 204/406

[58] Field of Search ............... 204/129.43, 141.5, 147, 204/284, 401, 402, 406, 415, 433, 153.21, 153.17

[56] References Cited

U.S. PATENT DOCUMENTS

| | | | |
|---|---|---|---|
| 4,772,375 | 10/1988 | Wullschleger et al. | 204/402 |
| 4,900,422 | 2/1990 | Bryan et al. | 204/401 |
| 5,032,245 | 7/1991 | Gemelli et al. | 204/242 |

FOREIGN PATENT DOCUMENTS 53-85496 7/1978 Japan .................... 204/406

OTHER PUBLICATIONS

Plambeck, J. A., Electroanalytical Chemistry Basic Principles and Applications, 1982, John Wiley & Sons, New York, p. 27.

Primary Examiner—Donald R. Valentine
Assistant Examiner—Mark Bender
Attorney, Agent, or Firm—Macdonald J. Wiggins

[57] ABSTRACT

A device for in situ cleaning a fouled membrane of a sensor disposed in an aqueous process solution includes a first electrolysis electrode disposed in the process solution immediately adjacent the membrane, a second electrolysis electrode disposed in the process solution and spaced apart from the first electrolysis electrode, and a controllable power source for passing a current between said first and second electrodes. The current produces a heavy concentration of ions at a surface of the fouled membrane. The polarity of the current is selectable to produce negative or positive ions for reacting to decompose deposited salts, or to scrub contaminates from the membrane surface.

10 Claims, 2 Drawing Sheets

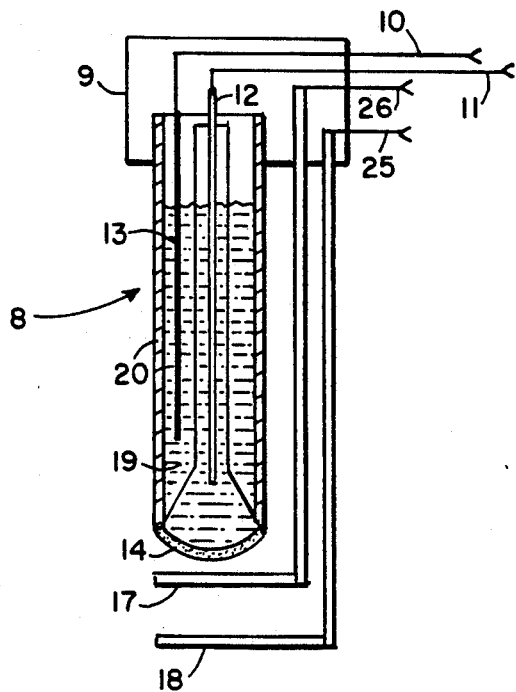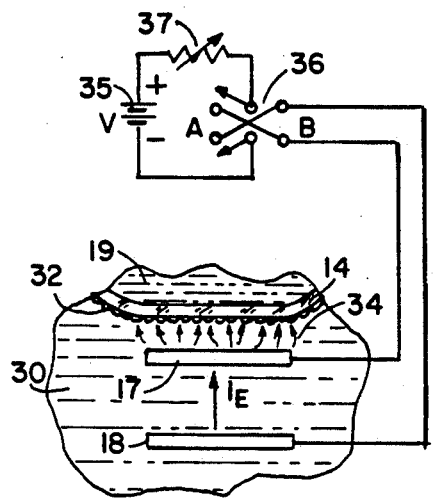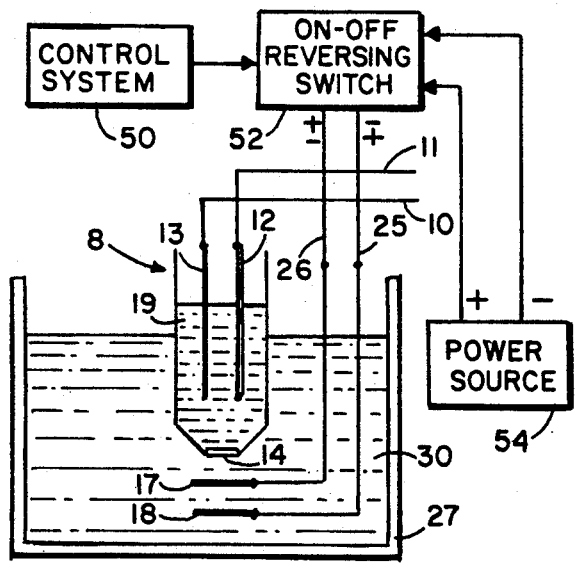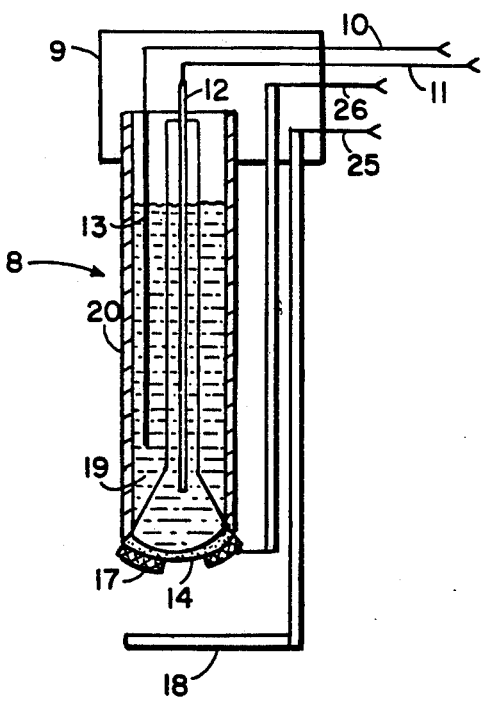

DEVICE FOR IN SITU CLEANING A FOULED SENSOR MEMBRANE OF DEPOSITS

FIELD OF THE INVENTION

The present invention relates to a sensor, such as a pH or dissolved oxygen (DO) sensor, operating in a process solution containing water, and more particularly to a system for in situ cleaning a membrane of the sensor fouled by cellular growth, oil films or salt precipitates on the membrane of the sensor.

BACKGROUND OF THE INVENTION

Organic and inorganic processes commonly require the use of sensor systems having a sensor in the process solution. For example, in many processes, the pH of the process must be continuously measured. In other processes the amount of dissolved oxygen is critical, and must be continuously monitored. Both pH and DO sensors have a membrane separating the sensor electrolyte from the process solution, while other sensors include optical windows. A major problem in such systems is the fouling of the sensor membrane or window. In organic processes containing cellular growth products, growth of cells on the sensor membrane may occur, causing incorrect sensor readings, as well as failure of the sensor. Other processes may deposit oil or other contaminant films on the membrane. In a process solution having significant hydroxide concentrations, common salts, such as copper, iron, or calcium precipitate on the sensor membrane.

In the prior art, fouling of the sensor has been corrected by halting the process, removing the sensor for cleaning, and thereafter replacing the sensor. Known on-line cleaning technology has proved to be expensive and not very reliable. Thus, there is a need for apparatus and method for quickly, accurately, and economically cleaning fouled sensors in situ.

SUMMARY OF THE DISCLOSURE

The present invention is applicable to pH sensors, and to DO sensors. The sensor is installed with the membrane portion extending into the process solution according to normal practice. Two electrodes are installed in the process solution external and adjacent to the sensor membrane. A first one of the electrodes is disposed immediately adjacent the membrane. Alternatively, the first of the two electrodes may be mounted directly on the surface of the pH sensor glass membrane and in the form of a conductive open grid. The second electrode is located adjacent the first electrode at a distance of about one fourth inch or more therefrom. The two external electrodes are connected to a current source by a polarity reversing switch so each can function interchangeably as an anode or a cathode. A predetermined controlled direct current from the source is periodically passed from anode to cathode through the solution for a short controlled period of time.

The current produces an electrolytic action in the aqueous solution. The major electrochemical reaction is electrolysis of water. In the case in which the first electrode is attached directly to the surface of the sensor membrane, the electrolysis and the resulting pH change are confined to a static layer of the solution directly at the membrane-layer interface. This layer defines a fixed volume, permitting the ability to step to a predetermined pH level. The electrolysis produces either an increase or a decrease in pH or oxygen concentration, in accordance with the direction of current flow through the solution.

When the current direction causes the electrode at the surface of the membrane to act as a cathode, a base is produced. When the membrane electrode acts as an anode, an acid is produced. As will be recognized, very high or very low pH levels will kill cellular growth on the membrane. The hydrogen and oxygen gas bubbles from the electrolysis of the process solution at the sensor membrane will then remove the fouling materials. It has been found that a one minute electrolysis period is sufficient to clear the fouling.

It is therefore a principal object of the invention to provide a system having real time, on-line means for periodic cleaning of a pH, DO, or other sensors having a fouled membrane.

It is another object of the invention to provide a system for use with a pH or DO sensor in an aqueous process solutions by periodically producing a controlled increase or decrease in pH of a volume of the solution to remove build up of cellular growths, oil, or common salts on the permeable membrane of the sensor.

It is still another object of the invention to provide a system for producing very high and very low pH in aqueous process solutions adjacent the membrane of a pH or DO sensor in the solution to kill and remove cellular growth on the membrane, to dissolve common salt precipitates from the membrane, and to scrub such deposits from the membrane.

These, and other objects and advantages of the invention, will be apparent from the following detailed description when read in conjunction with the drawings.

BRIEF DESCRIPTION OF THE DRAWINGS

FIG. 1 is a cross sectional view of a pH or DO sensor with a pair of external electrolysis electrodes adjacent the sensor membrane in accordance with the invention;

FIG. 2 is a partial view of the sensor and electrodes of FIG. 1 illustrating electrolysis in a process solution from an externally produced current for cleaning deposits from the sensor membrane;

FIG. 3 is an alternative arrangement of the sensor and electrodes of FIG. 1 in which one electrode is attached to the sensor membrane;

FIG. 4 is a schematic and block diagram of a typical pH or DO sensor in a process solution, and a system for periodically producing electrolysis by current through the external electrodes.

DETAILED DESCRIPTION OF THE PREFERRED EMBODIMENT

Figure 5:
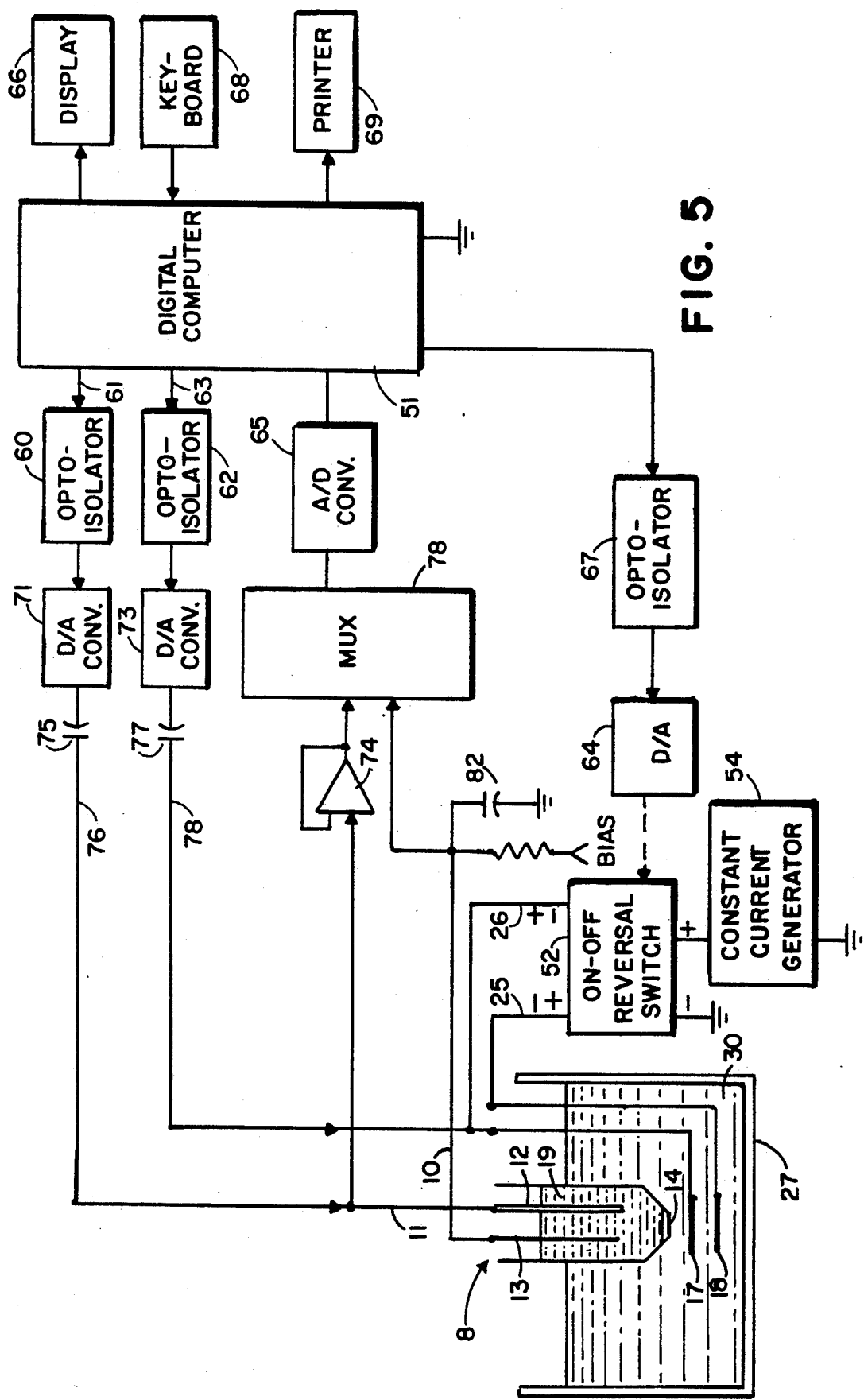
FIG. 5 is a block and schematic diagram of a system using the cleaning system of the invention, in combination with an ion measuring and monitoring system.

The invention is a system having means for removing fouling deposits on the permeable membrane of a pH or DO sensor immersed in an aqueous process solution. A typical prior art sensor 8 is shown in cross section in FIG. 1. Two external electrolysis electrodes 17, 18 are disposed adjacent membrane 14. The sensor 8 is mounted to a bracket 9 from which external metallic electrode 18 depends. A second external metallic electrode 17 is disposed immediately adjacent permeable membrane 14.

The reference electrode 13 and sensor electrode 12 of sensor 8 are selected in accordance with the type of measurement desired, as is electrolyte 19. Electrodes 13 and 12 are disposed in a housing 20 having an open lower end. The sensor membrane 14 is formed from material suitable to the application. Electrode 17 functions as a cathode or anode as determined by the polarity of a voltage applied across leads 25, 26. Test electrode 18 also functions either as an anode or cathode, and is spaced a shortdistance from test electrode 17. The distance is not critical but is normally more than 0.25 inches. Test electrodes 17 and 18 can be of any suitable material; preferably, platinum. As will be noted, reference electrode 13 of sensor 8 is connected to lead 10, and sensor electrode 12 connects to lead 11.

Turning now to FIG. 2, the lower portion of sensor 8 is shown immersed in process solution 30. Membrane 14 is indicated with a fouling deposit 32 thereon. A source of current is provided by voltage source 35 and variable resistance 37. It is to be understood that this current source is shown only for explanatory purposes, and other sources are equally suitable. Reversing switch 36 is in a center, non-operated position during normal operation of the pH or DO measurement system. When cleansing of the membrane 14 is required, The switch is closed to either position A or position B, in accordance with the need for basic ions or acidic ions to neutralize fouling deposit 32. In the example shown, switch 37 is assumed to be in position B, causing a current $I_E$ to flow from electrode 18 to electrode 17. Thus, electrode 17 is acting as a cathode, producing ions 34.

With switch 36 in position B, the current direction is such that electrode 17 at the surface of sensor membrane 14 is negative relative to electrode 18. In solution 30, the reaction at the membrane surface produces, for each one molecule of hydrogen, two negative hydroxide ions. Thus, the solution, at the membrane, becomes more basic. With the switch in position A, electrode 17 is positive. The reaction produces, for each oxygen molecule, four positive hydrogen ions. The solution at the sensor now becomes more acidic. These changes in pH are in agreement with either the Bronsted theory of acidity (acid=source of protons; base=acceptor of protons) or the Lewis theory of acidity (acid=electron pair acceptor, base=electron pair donor). See Reference 1, pp 496–9. Generally, current $I_E$ is selected to produce a pH in solution 30 greater than 12, or less than 2.

FIG. 3 illustrates an alternative arrangement of electrode 17. Electrode 17 is attached to a portion of the external surface of membrane 14, and is formed as a grid so as not to interfere with normal diffusion through membrane 14. Advantageously, the electrolysis action takes place directly on the membrane 14, enhancing the scrubbing action of the hydrogen and oxygen bubbles in removing fouling deposits therefrom.

A block and schematic diagram of the system of the invention is shown in FIG. 4. A process solution 30 for which the oxygen concentration or pH is to be measured is shown in a tank 27. A sensor 8 is shown immersed in the solution 30. External electrolysis electrodes 17, 18 are disposed adjacent membrane 14, and connected by leads 25, 26 to a controllable on-off reversing switch 52. Leads 25 and 26 may be open, or of either polarity. Switch 52 is controlled by a control system 50, which may include a timer to periodically operate switch to the ON position, and to control the polarity of the current thereby caused to flow between electrodes 17, 18. The timing may be set in accordance with an observed necessity for de-fouling membrane 14.

A power source 54 supplies the current for the electrolysis operation.

Control system 50 may include a computer programmed to interrupt operation of a pH or DO measurement system of the sensor, and to time and control the electrolysis cleaning procedure at preselected intervals, or upon sensing of membrane fouling. In U.S. Pat. No. 4,822,456; U.S. Pat. No. 4,900,422, and U.S. Pat. No. 4,961,163, computer systems are disclosed that provide means for displaying a reading from respective sensors, for continuously monitoring the impedance and/or dynamic characteristics of a membrane of a sensor, for detecting changes or deterioration in the sensor, such as fouling of the membrane, and for automatic on-line recalibration of the sensor. The present invention is applicable to such computer controlled measurement systems. Referring to FIG. 5, a block diagram of a typical system of this type is shown.

An ion or other type sensor 8 in process solution 30 has reference electrode 13 and sensing electrode 12 connected to a computer system having computer 51. Computer 51 is programmed to drive electrode 17, when not being used for membrane cleaning, to pass a first pseudorandom low frequency signal on lead 76 through membrane 14 to computer 51 via buffer 74, multiplexer 78, and A/D converter 65. The computer measures the current to determine the impedance of membrane 14 as explained in detail in U.S. Pat. No. 4,822,456, which is incorporated herein by reference. A second, non-correlated pseudorandom current is passed through ion electrode 12 to monitor the condition of that electrode. Computer 51 cross correlates the signals to separate the measurements.

When the impedance on membrane 14 is found by computer 51 to be out of tolerance, indicative of fouling, the computer then energizes switch 52 via D/A converter 64 as previously discussed. The cleaning process may be instituted cyclically, until a correct impedance is obtained. A computer program controls the electrolysis routine, and, when the impedance is within tolerance, recalibrates the system. Alternatively, a periodical cleaning may be programmed to prevent build up of fouling deposits.

As will now be recognized, a method of cleaning fouling deposits from a membrane of a sensor in a process solution is disclosed comprising the following steps:

a) providing a pair of electrolysis electrodes adjacent the membrane;

b) controlling a current through the solution to produce a highly basic or highly acidic condition at the membrane;

c) dissolving fouling deposits from the membrane; and d) flushing the deposits from the membranes.

Although the invention has been disclosed with reference to pH and DO measurement sensors, it is equally applicable to any type of sensor that is subject to fouling to permit in situ neutralization and cleaning of the fouling material. Various changes in the system can be made without departing from the spirit and scope of the invention.

REFERENCE

Donald I. Hamm, "Fundamental Concepts of Chemistry", Appleton-Century-Crofts, New York, N.Y., 1969.

We claim:

1. A device for in situ cleaning a membrane of a sensor fouled by deposits thereon, said membrane disposed in an aqueous process solution, comprising:
   a first electrolysis electrode disposed external to said membrane and in said process solution immediately adjacent said membrane;
   a second electrolysis electrode disposed external to said membrane and in said process solution, and spaced apart from said first electrolysis electrode; and
   means for passing a current between said first and second electrodes for producing a heavy concentration of ions at a surface of said membrane, whereby said ions neutralize and remove the deposits from said membrane.

2. The device as defined in claim 1 in which said current passing means includes:
   an electrical power source; and
   switching means having an OFF position, a first polarity position for causing said first electrode to act as a cathode, and a second polarity position for causing said first electrode to act as an anode.

3. The device as defined in claim 2 in which said switching means includes a control system for periodically operating said switching means.

4. The device as defined in claim 3 in which said control system is a computer.

5. The device as defined in claim 1 in which said first electrolysis electrode is attached to a portion of said membrane.

6. The device as defined in claim 5 in which said first electrolysis electrode is in form of a grid.

7. In a system for measuring pH or dissolved oxygen of an aqueous process solution having on-line monitoring of the impedance of a membrane of a sensor, said membrane disposed in said process solution, the improvement consisting of a device for in situ removal of fouling deposits on said membrane responsive to a change in said impedance, comprising:
   a first electrolysis electrode disposed on an external surface of said membrane and in said process solution;
   a second electrolysis electrode disposed in said process solution and spaced apart from said first electrolysis electrode;
   an electrical power source; and
   a polarity reversing switch having an OFF position, and connected between said power source and said first and second electrodes;
   whereby said switch in a first ION position passes a current between said first and second electrodes for producing a heavy concentration of basic ions at a surface of said membrane, and in a second ON position passes a current between said first and second electrodes for producing a heavy concentration of acidic ions at said surface of said membrane.

8. The improvement as defined in claim 7 which further comprises a control system connected to said switch for periodically operating said switch to said ON and OFF positions.

9. The improvement as defined in claim 7 in which said control system includes timing means.

10. The improvement as defined in claim 7 in which said control system includes:
    means for on-line measurement of an impedance of said membrane; and
    means for operating said control system responsive to a departure of said membrane impedance from a normal value caused by the fouling deposits of said membrane, to thereby remove the deposits.

* * * * *